US00PP21495P2

(12) United States Plant Patent
van Kleinwee

(10) Patent No.: US PP21,495 P2
(45) Date of Patent: Nov. 16, 2010

(54) ***OSTEOSPERMUM* PLANT NAMED 'OSECTRAWHI'**

(50) Latin Name: *Osteospermum ecklonis*
Varietal Denomination: Osectrawhi

(75) Inventor: Theodorus Cornelis Maria van Kleinwee, Zwaag (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/587,473

(22) Filed: Oct. 7, 2009

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent L Bell
(74) *Attorney, Agent, or Firm*—S. Matthew Edwards

(57) ABSTRACT

A new *Osteospermum* plant named 'Osectrawhi', particularly distinguished by its trailing, very vigorous growth habit, its white colored ray florets, facing upwards and its strong heat tolerance.

1 Drawing Sheet

Latin name of the genus and species of the plant claimed: *Osteospermum ecklonis*.

Varietal denomination: 'Osectrawhi'.

BACKGROUND OF THE NEW PLANT

The present invention relates to a new and distinct cultivar of *Osteospermum* plant, botanically known as *Osteospermum ecklonis*. The new *Osteospermum* is propagated by cuttings resulting from an open pollination of a proprietary *Osteospermum ecklonis* seedling selection as the female, or seed, parent identified as 'F0241-1', not patented. This pollination took place in The Enkhuizen, Netherlands, in 2004.

The new *Osteospermum* was discovered and selected as a single flowering plant within the progeny of the stated population grown in The Enkhuizen, Netherlands, in 2005. The new *Osteospermum* plant has been repeatably asexually reproduced by cuttings in The Enkhuizen, Netherlands since 2005. The distinctive characteristics of this new *Osteospermum* plant are stable and reproduced true to type in successive generations.

DESCRIPTION OF THE DRAWING

This new *Osteospermum* plant is illustrated by the accompanying photographic drawing which shows blooms, buds and foliage of the plant in full color, the color shown being as true as can be reasonably obtained by conventional photographic procedures.

SUMMARY OF THE INVENTION

Plants of the cultivar 'Osectrawhi' have not been observed under all possible environmental conditions. The phenotype may vary with variations in environment such as temperature and light intensity without, however, any variance in genotype.

The following traits have been repeatedly observed and are determined to be the unique characteristics of 'Osectrawhi.' These characteristics in combination distinguish 'Osectrawhi' as a new and distinct cultivar:

1. Trailing plant habit.
2. Strong vigor.
3. Clear white colored ray florets, facing upwards.
4. Strong heat tolerance.

In side-by-side comparisons conducted in The Enkhuizen, Netherlands, plants of the new *Osteospermum* differed from plants of the female parent selection in the following characteristics:

1. Female has a bigger inflorescence disk than 'Osectrawhi'.
2. Female has more upright and less vigorous plant type.
3. Female has bigger inflorescences.

TABLE 1

DIFFERENCES BETWEEN THE NEW CULTIVAR 'OSECTRAWHI' AND A SIMILAR CULTIVAR

| | 'OSECTRAWHI' | JAMBOANA ® Training White 'OSOSLAWIT(P) U.S. Plant Pat. No. 18,872 |
|---|---|---|
| Foliage margin shape, young leaves | Only occasionally serrated | Irregularly serrated |
| Plant habit | Very flat habit | Somewhat less flat habit |
| Color lower and upper side of petal | Clear white on upper side, white to purple shade, with blue stripes on lower side | Occasionally purple shade on upper side, more intense purple shade on lower side with less dominant stripes |

DESCRIPTION OF THE NEW CULTIVAR

The following detailed descriptions set forth the distinctive characteristics of this new *Osteospermum* plant The data which define these characteristics were collected from asexual reproductions carried out in The Enkhuizen, Netherlands. The plant history was taken on 21 week old plants. The instant plant was grown indoors in a 10.5 cm container and transplanted into the open field in week 20.

Color references are primarily to The R.H.S. Colour Chart of The Royal Horticultural Society of London, edition 2001. The plant:

*Classification—botanical.—Osteospermum ecklonis.*

Parentage:

*Female parent.*—Proprietary seedling selection 'F0241-1,' not patented.

*Male parent.*—Female is open pollinated so male is unknown.

Plant description:

*Growth habit.*—Round, trailing.

*Plant height.*—15 cm.

*Spreading area of plant.*—50 cm.

*Vigour.*—Very strong.

*Branching character.*—Freely branching, 14 lateral branches without pinching.

*Flowering period.*—From May until October.

The stem:

*Length.*—19 cm.

*Diameter.*—11 mm.

*Internode length.*—3-19 mm.

*Texture.*—Glabrous.

*Color.*—RHS 146D in young stem, RHS 146C when stem gets older. Older parts that are exposed to sunlight show anthocyanin, color RHS 187C.

The foliage:

*Arrangement.*—Single, alternate.

*Shape.*—Elliptic.

*Apex.*—Broadly acute.

*Base.*—Attenuate.

*Margin.*—Irregularly serrated in old leaves, only occasionally serrated in young leaves.

*Number of leaves per lateral branch.*—40-70.

*Texture.*—Glabrous, leathery.

*Color upper side.*—RHS 137C.

*Color lower side.*—RHS 137D.

*Length.*—First developed leaves: up to 7.5 cm; last developed leaves: up to 3.5 cm.

*Width.*—First developed leaves: up to 2.5 cm; last developed leaves: up to 1 cm.

*Petiole.*—Absent.

The inflorescence:

*Number of inflorescences per mature plant.*—25.

*Inflorescence bud.*—Shape: Ovoid. Length: 15 mm. Width: 10 mm. Color: RHS 144A.

*Inflorescence lastingness on the plant.*—Approximately 8 days, depending on temperature.

*Inflorescence diameter.*—60 mm.

*Inflorescence depth.*—10 mm.

*Disc diameter.*—9 mm.

*Fragrance.*—Absent.

*Disc florets.*—Shape: Tubular, elongated. Number of disc florets per inflorescence: 60. Length: 7 mm. Width: 1 mm. Apex: Five pointed. Color: N81C, N89C near apex. In young stage 95A.

*Ray florets.*—Shape: Capitulum with two series of ray florets. Number of ray florets per inflorescence: 18. Color upper surface: Whiter than RHS 155A. Color lower surface: White to purple shade: whiter than RHS 155A to RHS N81B. Longitudinal stripes RHS 94A. Length: 28 mm. Width: 6 mm. Apex: Rounded. Base: Acute. Margin: Entire. Texture: Satiny.

*Peduncles.*—Length: 6-10 cm. Texture: Sturdy; tiny hairs. Color: RHS 144A, with anthocyanin RHS 187C on parts that are exposed to sunlight. Diameter: 1.5 mm. Shape: Round.

*Phyllaries.*—Texture: Rough; tiny hairs. Number of phyllaries: 14-16. Color: RHS 144A. Length: 10 mm. Margin: Entire. Width: 1 mm. Apex: Acute. Shape: Ligulate.

Reproductive organs:

*Androecium.*—Presence: Present on disc florets only. Shape: Oblong; five stamens fused to one. Length: 3 mm. Width: 1 mm. Pollen color: RHS 17A.

*Gynoecium.*—Presence: Present on both ray and disc florets. Pistil number: One pistil per ray or disc floret. Pistil length: 4 mm. Stigma color: RHS 79A. Stigma shape: Bipartite.

Seed development: Seed development has been observed on plants of the new *Osteospermum.*

*Amount of seeds produced.*—Rather abundant.

*Seed length.*—6 mm.

*Seed diameter.*—3 mm.

*Seed color.*—Mature seed RHS 200A; immature seed RHS 144A.

*Seed shape.*—Elliptic.

Disease and pest resistance: No disease and pest resistance has been observed to date.

What is claimed is:

1. A new and distinct variety of *Osteospermum* plant named 'Osectrawhi', as substantially illustrated and described herein.

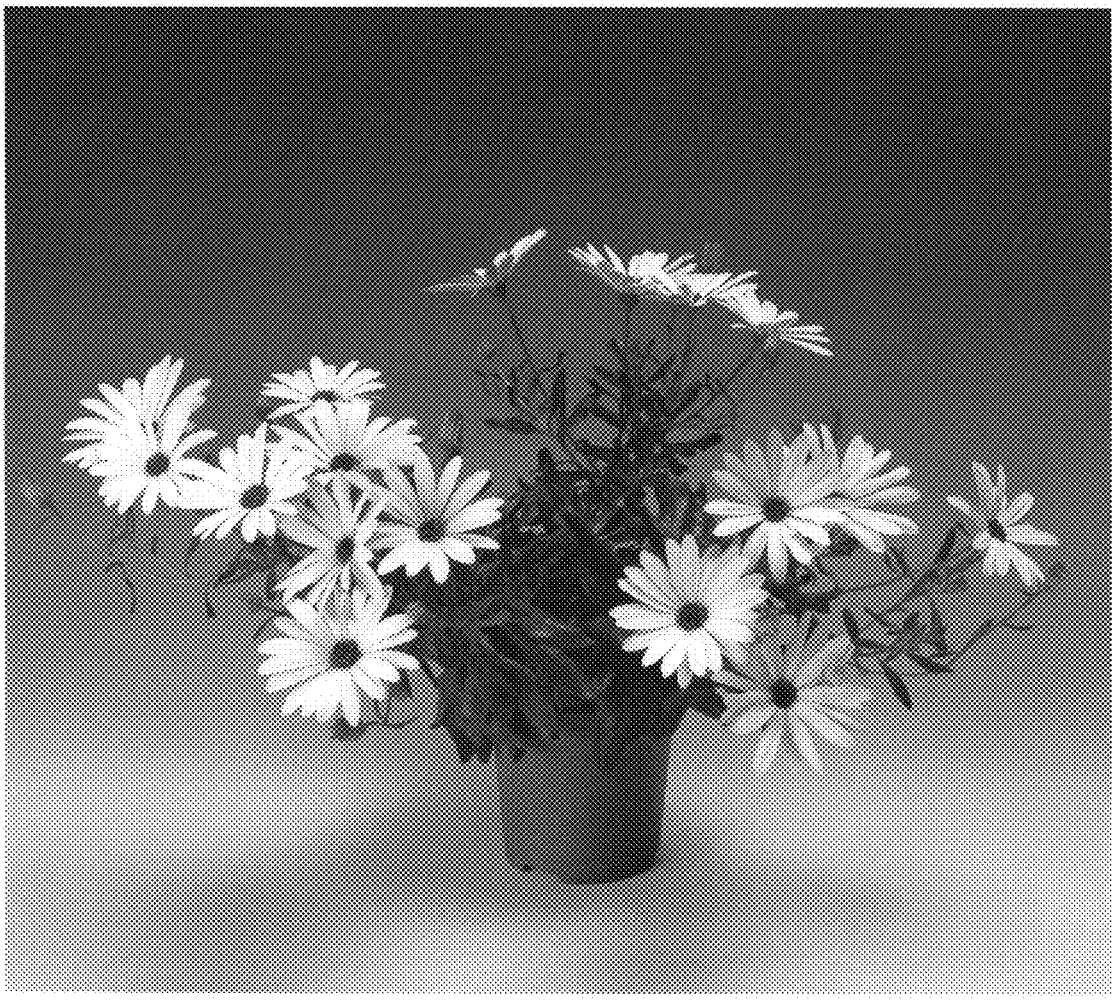

* * * * *